(12) United States Patent
Röhnert et al.

(10) Patent No.: US 7,858,655 B2
(45) Date of Patent: Dec. 28, 2010

(54) DRUG PREPARATION COMPRISING α-LIPOIC ACID, AMBROXOL AND/OR INHIBITORS OF THE ANGIOTENSIN-CONVERTING ENZYME (ACE) AND ITS USE FOR THE TREATMENT OF NEURODEGENERATIVE DISEASES

(75) Inventors: Peter Röhnert, Magdeburg (DE); Frank Striggow, Gerwisch (DE); Klaus Reymann, Niederndodeleben (DE); Siegfried Ansorge, Hohenwarte (DE); Michael Täger, Heinrichsberg (DE); Ulrich Schröder, Eussenheim (DE)

(73) Assignee: Keyneurotek Pharmaceuticals AG, Magdeburg (DE)

( * ) Notice: Subject to any disclaimer, the term of this patent is extended or adjusted under 35 U.S.C. 154(b) by 0 days.

(21) Appl. No.: 10/764,676

(22) Filed: Jan. 26, 2004

(65) Prior Publication Data

US 2004/0219207 A1   Nov. 4, 2004

(51) Int. Cl.
*A61K 31/40* (2006.01)
(52) U.S. Cl. .................................................... 514/412
(58) Field of Classification Search ................ 514/412; 548/452, 533; 549/39
See application file for complete search history.

(56) References Cited

U.S. PATENT DOCUMENTS

2002/0177558 A1   11/2002   Meyerhoff et al.

FOREIGN PATENT DOCUMENTS

WO   WO 02/096398 A2   12/2002
WO   WO 02/096414 A1   12/2002

OTHER PUBLICATIONS

Gillissen et al., Respiratory Med. (1998), vol. 92, pp. 609-623.*
Derick et al., Biochem. Biophy. Research Comm. (1995), vol. 207, No. 1, pp. 258-264.*
Elena et al., Am. J. Physiol. Regulatory Integrative Comp. Physiol., (2000), vol. 278, pp. R572-R577.*
Biewenga et al., Gen, Pharm, (1997), vol. 29(3), pp. 315-331.*
Jablonka, Stanislaw, Andrzej Ledwozyw, Wojciech Kadziolka, Andrzej Jablonka, and Andrzej Nestorowicz, "The Influence Of Ambroxol On Peroxidative Processes In Lung And Plasma In Dogs After Pulmonectomy," *Archivum Veterinarium Polonicum*, 1992, pp. 57-66, vol. 32, No. 1-2.
Kozhevnikova, E.V. and L.M. Adzhienko, "Neuroprotective Activity Of Angiotensin-Converting Enzyme Inhibitors In Cerebral Ischemia," *Bulletin Of Experimental Biology And Medicine*, 1999, pp. 1122-1124, vol. 11.
Packer, Lester, Hans J. Tritschler, and Klaus Wessel, "Neuroprotection By The Metabolic Antioxidant α-Lipoic Acid," *Free Radical Biology & Medicine*, 1997, pp. 359-378, vol. 22, No. ½.
Ravati, Alexander, Vera Junker, Maria Kouklei, Barbara Ahlemeyer, Carsten Culmsee, and Josef Krieglstein, "Enalapril And Moexipril Protect From Free Radical-Induced Neuronal Damage In Vitro And Reduce Ischemic Brain Injury In Mice And Rats," *European Journal Of Pharmacology*, 1999, pp. 21-33, vol. 373.
Stoll, S., A. Rostock, R. Bartsch, E. Korn, A. Meichelböock, and W.E. Müller, "The Potent Free Radical Scavenger α-Lipoic Acid Improves Cognition In Rodents," *Annals New York Academy Of Sciences*, 1994, pp. 122-128.
Werner, Christian, William E. Hoffman, Eberhard Kochs, Sara F. Rabito, and David J. Miletich, "Captopril Improves Neurologic Outcome From Incomplete Cerebral Ischemia In Rats," *Stroke*, Jul. 1991, pp. 910-914, vol. 22, No. 7.

* cited by examiner

*Primary Examiner*—Taofiq A Solola
(74) *Attorney, Agent, or Firm*—Hodgson Russ LLP

(57) ABSTRACT

The present invention concerns the use of Provided is a drug composition and a method for using the composition for the prevention and the therapy of neurodegenerative diseases. The combination comprises at least two of the following substances: α-lipoic acid; ambroxol and one or several inhibitor(s) of the angiotension-converting enzyme (ACE).

14 Claims, 3 Drawing Sheets

Figure 3
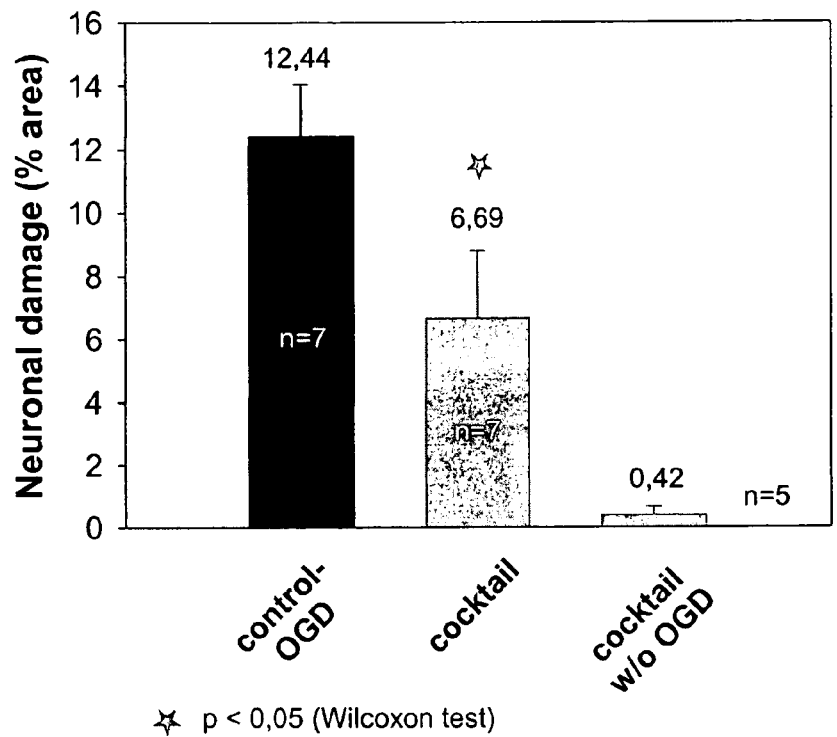
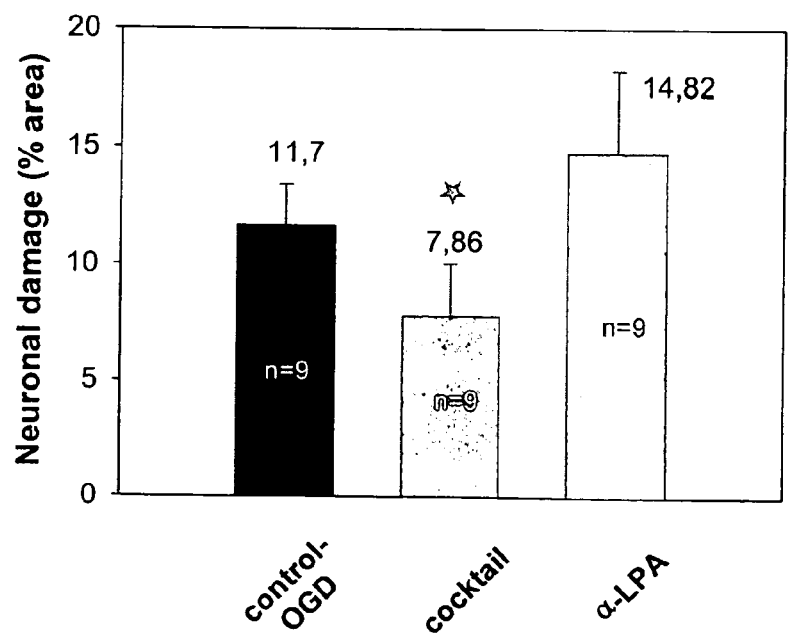
Fig. 4a)

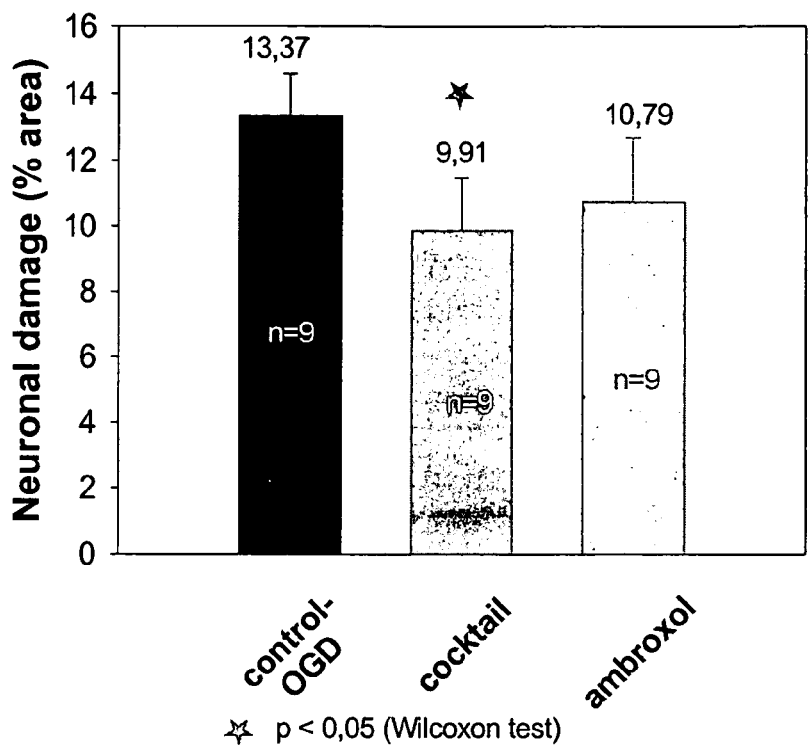
Fig. 4b)  ☆ p < 0,05 (Wilcoxon test)
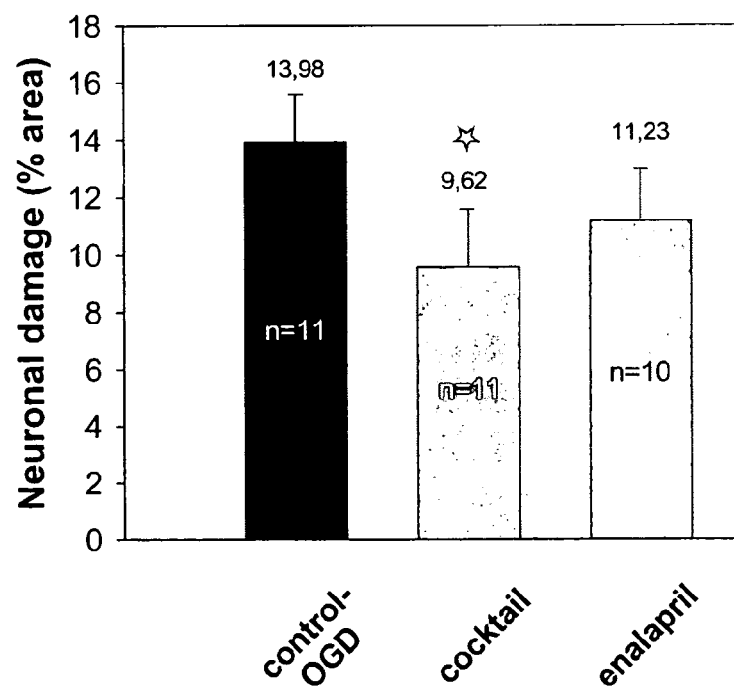
Fig. 4c)  ☆ p < 0,05 (Wilcoxon test)

DRUG PREPARATION COMPRISING α-LIPOIC ACID, AMBROXOL AND/OR INHIBITORS OF THE ANGIOTENSIN-CONVERTING ENZYME (ACE) AND ITS USE FOR THE TREATMENT OF NEURODEGENERATIVE DISEASES

BACKGROUND OF THE INVENTION

The invention relates to a drug preparation which comprises α-lipoic acid, ambroxol and/or an ACE inhibitor (inhibitor of the angiotensin-converting enzyme). Furthermore, the invention relates to the use of a drug preparation for therapeutically treating degenerative diseases of the Central Nervous System (CNS) as, for example, ischemic or hemorrhagic stroke, focal or global ischemia, amyotrophic lateral sclerosis (ALS), Alzheimer's disease, Parkinson's disease, Hunntington's disease, Multiple Sclerosis, neurodegeneration of the aged and age-related dementia, trauma and Autosomal Dominant Neurohypophyseal Diabetes Insipidus (ADNDI). Included in the invention is also a use of the preparation according to the invention for the prevention and therapy of cerebral ischemia following cardial and cardiovascular insults. The above-mentioned clinical indications lead to a loss of the function of certain areas of the CNS and result, in almost all cases, into an irreversible mental and physical handicap. A regulative intervention into the cellular thiol status in cases of neurodegenerative diseases intends, on the one hand, to minimize the generation of damage and, on the other hand, to prevent damage in cases of less severely damaged cells in the penumbra.

The cellular thiol/disulfide status is one of the most important basic preconditions of biological metabolic performance. Particularly, the functionality of proteins is influenced to a large extent by the oxidation and reduction of thiol/disulfide groups.

The maintenance and proper function of the metabolism of cleaving disulfide groups and generating thiol groups as controlled by several classes of different enzymes is indispensable for the cell viability in view of its manifold biological functions, inter alia in processes of cellular growth and differentiation including the programmed cell death as well as mechanisms of cell protection and cell decontamination. Disturbances in this metabolic system and changes of the thiol concentration result into severe functional disturbances of the cell which can be restricted locally only in individual cases; usually, such disturbances adversely affect large parts of the tissues concerned and even extend to adjacent tissues or to the whole organism.

The role of a disturbed thiol/disulfide status in the cell, during the generation of neurodegenerative diseases and during their progress as well, was not sufficiently explored, up to now. Hence, there is an urgent need to elucidate the connections between thiol status and the pathophysiology of neurodegenerative diseases, particularly with the aim of finding potent effective agents for the treatment of diseases and damage of the central nervous system for which an equivalent medicament intervention is not yet available up to now.

In the course of a degeneration of neurons after ischemic events, the inhibition of endogenic protection mechanisms plays a vital role, in addition to a damage of the endothelium (change of the barrier function of the blood brain barrier), since many enzymes and regeneration systems are inhibited subsequent to the ischemia [1, 2]. This can be realized particularly during the reperfusion phase.

Not only in cases where a person is affected by a stroke, but also in cases where other neurodegenerative diseases occur, i.e. diseases having an acute or a chronic course, as, for example, Parkinson's disease, Alzheimer's disease [3], aging processes [4, 5], hemorrhagic stroke [6], excitotoxicity [7], ALS and trauma [8], a neuronal damage as a consequence of a lack of protection or regeneration systems or of their inhibition is discussed. It could not yet be elucidated what is the actual contribution thereof. If, however, partial components of those endogeneous protection systems are defect or are present only to a minor extent, as shown here for the example of pyramidal cells, this may have dramatic consequences.

A lack of cellular protection mechanisms results, inter alia, into lipid peroxidation, as a consequence of which the integrity of cellular membranes is lost. By such a mechanism, membrane-bound proteins are affected. In cases of ischemia, for example, glutamate-transporting proteins are affected functionally [8], the function of which is to transport released glutamate back into the cell and to thereby prevent a toxic extracellular concentration of this neurotransmitter molecule from occurring.

α-lipoic acid is used with moderate success up to now as an adjuvant for the treatment of mis-sensations in the frame of peripheric diabetic polyneuropathia (Diabetologica 1995; 38: 1425-1433; Diabetes Res. Clin. Pract. 1995; 29: 19-26; Diab. Care 1999; 22: 1296-1301; Drug Metab. Rev. 1997; 29: 1025-1054; DE 43 43 592 C2). Moreover, in the patent documents DE 44 47 599 C2 and EP 0 530 446 B1, the use of α-lipoic acid for the treatment of further neuronal disturbances as, for example, tinnitus and sudden deafness is protected.

The cytoprotective mechanism in the course of symptoms accompanying diabetes is based not only on influencing the sugar-dependent modification of proteins (glycosylation of proteins) and on decreasing the genesis of toxic ketone bodies, but also on the function of α-lipoic acid and its metabolites as antioxidants [9].

In the patent documents EP 0 812 590 A2 and EP 0 427 247 B1, the use of α-lipoic acid as a peripheric cytoprotective agent, an anti-analgesic agent and as a medicament against inflammation diseases is disclosed.

Ambroxol (trans-4-(2-amino-3,5-dibromobenzylamino-)cyclohexane hydrochloride) is used in several different administration forms as a mucolytical medicament for lung and bronchial diseases (WO 96/33704; GB 2,239,242; WO 01/05378). Moreover, its use against hyperuricemia is known from the document DE 35 30 761. The effect of ambroxol as a mucolytical agent is based on a stimulation of the surfactant production of bronchial cells and, particularly, on its capability of eliminating free radicals as well [10]. The antioxidative activity of said substance based thereon was primarily detected at pulmonal cells [11], but also in the frame of inflammatory mechanisms [12]. Furthermore, it is known that regulatory enzymes of the glutathione metabolism are directly influenced by an addition of ambroxol in large doses [13].

Inhibitors of the angiotensin-converting enzyme (ACE) are very successfully used for the treatment of a broad spectrum of cardiovascular diseases. This class of substances provides their blood pressure-decreasing effect via an inhibition of the transformation of angiotensin-I into angiotensin-II and via an influence on the kinine metabolism, respectively. For influencing intracellular redox processes, one has to distinguish the effects of ACE inhibitors bearing thiol groups as, for example, Captopril (1-[(2S)-3-mercapto-2-meth-ylpropio-nyl-]L-proline) from the effects of thiol-free ACE inhibitors as, for example, Enalapril (1-{N-[(S)1-ethoxycarbonyl-3-phenylpropyl-]L-alanyl-}L-proline). While the former react directly as radical scavengers and, hence, have an antioxidative effect, the latter SH-free ACE inhibitors are not able to do so primarily. However, a common feature of both groups is their influence on the glutathione redox cycle via a regulation of the glutathione reductase, of the glutathione peroxidase and of the superoxide dismutase (Am. J. Physiol. Regulatory Integrative Comp. Physiol. 2000; 278: 572-577).

Already in the document DE 44 20 102 A1, the use of different medicaments in combination with α-lipoic acid was protected for the improvement of existing drug therapies against cardiovascular and diabetes-caused diseases. The claims of this patent are restricted to those areas of use, with the exception of the combination of α-lipoic acid and calcium antagonists which are not a part of the presently described novel substance combination. In the document DE 44 20 102 A1, the use of a combination of α-lipoic acid and calcium antagonists is claimed for neurodegenerative diseases, exclusively. Subject-matter of the main claim of the document DE 44 20 102 A1 is the differentiation of the different stereoisomers of α-lipoic acid as specifically useable effective agents and specified drug formulations.

SUMMARY OF THE INVENTION

In contrast thereto, the present invention claims novel substance combinations and medicaments on their basis for reducing neuronal damaging processes as a cause of, and in sequence to, neurodegenerative diseases. The development of novel neuroprotective medicaments was made on the basis of substances which positively influence the thiol/disulfide status of cells in the central nervous system (CNS). Since presently no valid medicament prevention and therapy of neurodegenerative diseases is available (neither therapeutic nor symptomatic), the presently described invention potentially opens a large pharmaceutical potential.

Indeed, the basis of the present invention is the novel finding that neurons are provided with a lower content of free (reduced) thiol groups, which fact causally influences their vulnerability towards degenerative insults negatively. Surprisingly, it could be shown that a marked reduction of cerebral damage after degenerative events/insults can be achieved by a combination of two or more substances of the group of α-lipoic acid, its salts and isomers, ambroxol and its salts and prodrugs and at least one inhibitor of the ACE. Potentially, there was found a promising proposal for a prevention and therapy of neurodegenerative diseases which could not be treated, or could only unsufficiently be treated, up to now.

BRIEF DESCRIPTION OF THE DRAWINGS

FIG. 3 is a graph illustrating the effect of the combination of α-lipoic acid, ambroxol and Enalapril on the survival of neuronal cells after OGD; and FIGS. 4a), 4b) and 4c) are graphs similar to FIG. 3 illustrating a comparison of the combined use of the combination with the effects of the single components.

DETAILED DESCRIPTION OF THE INVENTION

Figure 1A:
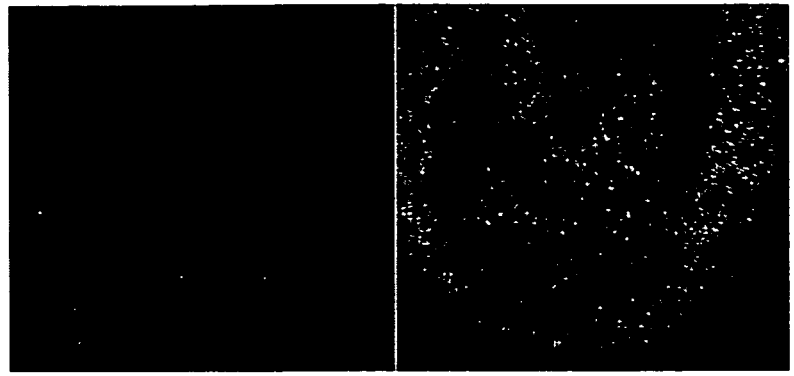
FIGS. 1a and 1b are histochemical fluorescence photographs illustrating organotypical hippocampal tissue cuts.

In the frame of the research leading to the present invention, there could be found the surprising fact that the intracellular thiol/disulfide metabolism plays an enormous role in the course of the pathogenesis of neurodegenerative diseases. It could be demonstrated in the present experiments that the extremely vulnerable nervous cells (neurons) of the CNS are provided with a lower content of free thiols less vulnerable than non-neuronal cells (as, for example, astrocytes and glia cells). This can be seen very clearly from the histochemical fluorescence photographs of FIGS. 1a, b, or, on a neuronal level, from the FIGS. 2a, b. Furthermore, and on the basis of these findings, the important role of thiol-reactive compounds as a protection mechanism in the course of neurodegeneration could be shown by the controlled influence on the cellular thiol/disulfide status by means of two or more substances of the group α-lipoic acid, its salts and isomers and modulators of the glutathione metabolism (ambroxol and its salts and prodrugs and an inhibitor of the ACE).

Surprisingly, by the combination of two or more substances of the group α-lipoic acid, its salts and isomers, ambroxol and its salts and prodrugs and at least one inhibitor of ACE, the survival of neurons after a neurodegenerative insult could significantly be improved successfully in the experiments described. In contrast to these results, an application of a single one of the above substances had no effect. In the present experiments, there was measured the ratio of degenerating neurons, which is a clinically extraordinarily relevant parameter.

Hence, the invention relates to pharmaceutical preparations comprising two or more substances of the group α-lipoic acid and its salts and isomers, ambroxol and its salts and prodrugs and at least one inhibitor of the angiotensin-converting enzyme (ACE), optionally together with usual pharmaceutically acceptable carriers, additives and adjuvants.

The invention also relates to the use of such a pharmaceutical preparation comprising two or more substances of the group α-lipoic acid and its salts and isomers, ambroxol and its salts and prodrugs and at least one inhibitor of the angiotensin-converting enzyme (ACE), optionally together with usual pharmaceutically acceptable carriers, additives and adjuvants, for the prevention and therapy of neurodegenerative diseases.

Hence, the correction of a disturbed thiol metabolism by α-lipoic acid, ambroxol and/or an inhibitor of ACE achieves a basic importance for the prevention and therapy of a plurality of diseases having a different genesis, particularly, however, in view of preventive and of therapeutic methods of treatment of neurodegenerative diseases. Without wanting to be fixed to one theory, it is assumed that the effect of the compounds described herein is optionally based on their thiol-stabilising effect, whereby surprisingly synergistic neuroprotective effects could be induced by the present new and targeted combination of agents. In contrast thereto, the application of single substances was basically without effect.

The selected experimental conditions were very largely in accordance with a clinical situation [14, 15]. All compounds tested were drugs already having a clinical admission. Thus, the test of security clearance of the single substances was already performed successfully. All single substances, and the substance combinations as well, showed no neurotoxic properties.

In accordance with the present invention, the pharmaceutical preparations with the features of claim 1 are claimed. In other words: The present invention comprises the combination of any two of the above effective agents as well as the combination of all three effective agents. Preferable embodiments can be derived from subclaims 2 to 9. Claim 10 claims the use of the preparations of the invention in one area of indication. Preferable embodiments of those uses can be derived from the dependent claims 11 and 12.

One component of the pharmaceutical compositions according to the invention may be α-lipoic acid. The term "α-lipoic acid" in accordance with the present invention is understood to comprise the pure compound α-lipoic acid (the name of which compound, according to the terminology, is (R)-5-(1,2-dithiolane-3-yl-)pentanoic acid) and its salts as well; however, in the present case, only pharmaceutically acceptable salts are covered. The term "α-lipoic acid" is considered to also comprise the stereoisomer and mixtures of the two isomers and the racemic mixture as well. The term "α-lipoic acid" is considered to also comprise each metabolite of α-lipoic acid, including oxidized and reduced forms of said acid. Combinations of said α-lipoic acid substances may be used as well.

One of the effectors of the glutathione metabolism and a component useable in the pharmaceutical compositions according to the invention is ambroxol of the general formula I:

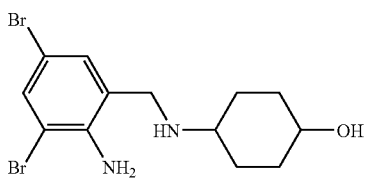

I

Ambroxol is used as such or—preferably—in the form of a salt and/or a prodrug thereof. Only pharmaceutically acceptable salts can be used. The term "prodrugs of ambroxol" is considered to comprise, in the frame of the present invention, all substances which may be applied and/or administered as a precursor of said compound and are transformed ("activated") into the active agent in the body, for example when acted on by an enzyme.

As the second effector of the glutathione metabolism and as another conceivable component of the pharmaceutical compositions of the present invention, there is used one inhibitor (or there are used several inhibitors) of the angiotensin-converting enzyme (ACE). There may be used all per se known inhibitors of the angiotensin-converting enzyme. Examples are enalapril, captopril, lisopril, ramipril and spirapril, without the invention being restricted to those. In the meantime, a plurality of molecule variants is available which may be distinguished primarily in their pharmacokinetic properties while having a similar pharmadynamic profile.

In view of the results obtained, the presence of free thiol groups in the molecule is no precondition for the efficacy, since comparable experimental data were achieved when using a thiol group-free ACE inhibitor. In accordance with the present invention, the following compounds may be used preferably:

A) 1-[(2S)-3-Mercapto-2-methylpropionyl-]L-proline (Captopril) having the general formula II

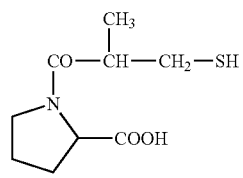

II

B) 1-{$N^2$-[(S)-1-Carboxy-3-phenylpropyl-]L-lysyl-}L-proline (Lisinopril) having the general formula III

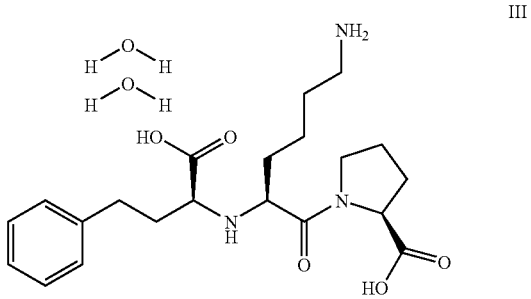

III

C) 1-{N-[(S)-1-Ethoxycarbonyl-3-phenylpropyl-]L-alanyl-}L-proline (Enalapril) having the general formula IV

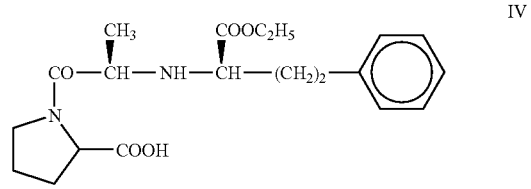

IV

D) (2S,3aS,6aS)-1-{(S)-N-[(S)-1-Ethoxycarbonyl-3-phenylpropyl-]alanyl-}-octahydrocyclopenta[b]-pyrrol-2-carboxylic acid (Ramipril) having the formula V

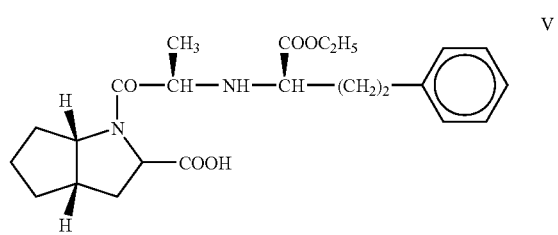

V

Also included are, for example, compounds wherein proline was substituted, modified or replaced:

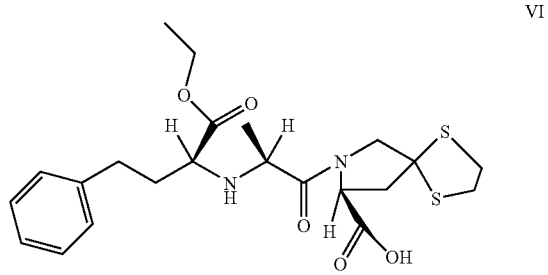

VI

Spirapril (8S)-7-{(S)-N-[(S)-1-Ethoxycarbonyl-3-phenyl-propyl-]alanyl-}-1,4-dithia-7-azaspiro[4,4]nonane-8-carboxylic acid;

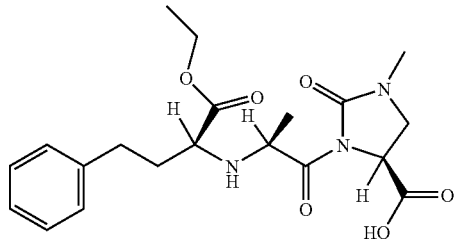

VII

Imidapril (4S)-3-{N-[(S)-1-Ethoxycarbonyl-3-phenylpropyl-]L-alanyl-}1-methyl-2-oxo-4-imidazolidine carboxylic acid;

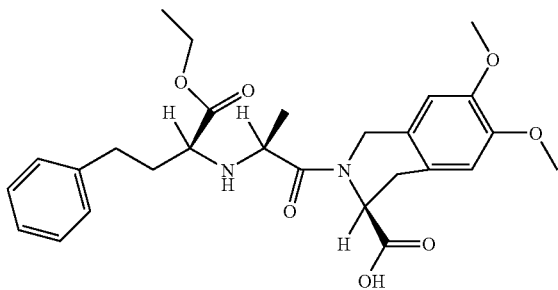

VIII

Moexipril (3S)-2-{N-[(S)-1-Ethoxycarbonyl-3-phenyl-propyl-]L-alanyl-}1,2,3,4-tetrahy-dro-6,7-dimethoxy-3-isochinoline carboxylic acid.

In cases of administering the above compounds, the preferred dose for a medical application to a human is dependent upon the compound used.

In the pharmaceutical compositions according to the invention, the substances of the above-mentioned groups may be contained in each desired combination. Preferred examples according to the invention are combined pharmaceutical preparations containing α-lipoic acid, its salts, stereoisomers or metabolites and ambroxol, its salts or its prodrug(s) in combination or containing α-lipoic acid, its salts, stereoisomers or metabolites and one or several inhibitor(s) of the angiotensin-converting enzyme in combination or containing one or several inhibitor(s) of the angiotensin-converting enzyme and ambroxol, its salts or its prodrug(s) in combination or containing α-lipoic acid, its salts, stereoisomers or metabolites and ambroxol, its salts or its prodrug(s) and one or several inhibitor(s) of the angiotensin-converting enzyme in combination.

The amounts of the aforesaid components contained in the compositions of the invention may be varied within broad limits and are primarily conditional on the facts found by a skilled person in a patient to whom the composition is to be administered. The kind and severity of the disease, the status of the patient, the body weight and metabolism parameters of the patient and the selected route of administration are important variables of the amounts to be administered. The effective dose of α-lipoic acid or its salts or isomers—as the effective doses of the other component(s) contained in the pharmaceutical composition according to the invention—has to be determined along the facts of the case and is decisively dependent on the usual doses for known fields of application and on patient-related parameters as well, for example on the above-mentioned parameters.

In preferred embodiments of the invention, the compositions for use in human-medical applications to a patient comprise α-lipoic acid in amounts of from 30 to 1,200 mg/day, particularly preferred in amounts of from 200 to 600 mg/day. The afore-mentioned doses are doses per day, which may be administered in a single dose per day or in any number of doses per day, most preferably in up to three single doses per day. The dose of ambroxol for a human-medical application is preferably between 7.5 and 90 mg/day, particularly preferably between 60 and 75 mg/day, which doses are also doses per day, which may be administered in a single dose per day or in any number of doses per day, respectively, most preferably in up to three single doses per day. The dose of ACE inhibitors for a human-medical application is preferably between 1 and 50 mg/day, particularly preferably between 5 and 20 mg/day, which doses are also doses per day, which may be administered in a single dose per day or in any number of doses per day, respectively, most preferably in up to three single doses per day.

Additionally, the pharmaceutical compositions may contain usual carriers, additives and/or adjuvants, depending upon the area of application, administration form or upon further requirements. Those substances may comprise, for example, aqueous solvents, stabilizers, suspension agents, dispersion agents, wetting agents, disintegrants (in cases where an oral administration of the composition in the form of tablets is intended) as well as food supplements.

The pharmaceutical compositions according to the invention may be prepared by per se known methods in arbitrary formulations. For example, preferred formulations comprise solutions which may contain organic and/or inorganic solvents, granulates,: aerosols, powders, suspensions, emulsions, tablets (optionally to be chewed) and/or coated tablets, tablets having a slowed or delayed release of the effective agent(s), capsules as well as transdermal application systems. In such formulations, the components of the pharmaceutical composition according to the invention may be present either in a single formulation form or in separate formulation forms.

The combination preparations applied according to the invention may be administered in usual pharmacological administration forms either prophylactically or therapeutically. Conceivable administration forms are: tablets (tablets resistant to gastric juice, coated tablets), powders, granulates, capsules, solutions, emulsions, suspensions, aerosols, transdermal application systems, administration forms having a slowed or delayed release of one or of all of the effective agent(s) or administration forms having a non-delayed release of the agent(s). The components may be administered in spatially separated preparations. More-over, it is also possible that those separated preparations are administered in one formulation wherein concentration amounts of the single components which are in accordance with specific cases are administered in the form of tablets (tablets resistant to gastric juice, coated tablets), powders, granulates, capsules, solutions, emulsions, suspensions, aerosols, transdermal application systems, administration forms having a slowed or delayed release or a non-delayed release of one or of all of the effective agent(s).

The pharmaceutical compositions according to the invention may be administered on each arbitrary administration route. The following are non-restricting examples thereof: the oral, buccal, pulmonal, nasal, transdermal, intravenous, subcutaneous, intracutaneous, intramuscular, rectal, vaginal or intrathecal administration, optionally together with per se known carriers, adjuvants and additives as well as in combination with food supplements. The components may be administered in spatially separated preparations. Moreover, it is also possible that those separated preparations are administered in one formulation wherein concentration amounts of the single components which are in accordance with specific cases are administered for a systemic application as, for example, an oral, buccal, pulmonal, nasal, transdermal, intravenous, subcutaneous, intracutaneous, intramuscular, rectal, vaginal or intrathecal administration, optionally together with per se known carriers, adjuvants and additives as well as in combination with food supplements.

The pharmaceutical compositions of the invention containing two or more than two of the components mentioned above in detail are particularly suitable, in the meaning of the present invention, for the prophylaxis and treatment of degenerative diseases of the central nervous system (CNS). A treatment may be performed in such cases simultaneously, in separate formulations or in separate time stages periodically. Advantageously, the pharmaceutical compositions according to the invention may be used in the course of the prophylaxis and therapy of the following diseases: ischemic and hemorrhagic stroke, amyotrophic lateral sclerosis, Alzheimer's disease, Parkinson's disease, Hunntington's disease, multiple sclerosis, neurodegeneration of aged people, dementia, cranial cerebral trauma and Autosomal Dominant Neurohypophyseal Diabetes Insipidus (ADNDI). In further embodiments, the pharmaceutical composition of the present invention is also used for the prevention and therapy of cerebral ischemia resulting from cardial and cardiovascular insults.

The pharmaceutical compositions according to the invention comprising a combination of two or more substances of the group of α-lipoic acid, ambroxol and inhibitor of the angiotensin-converting enzyme and its use in the frame of a prophylaxis and therapy of degenerative diseases of the CNS is further described by the examples and Figures. The examples are presented only for purposes of illustrating preferred embodiments of the invention and do not serve as a restriction of the invention.

EXAMPLE 1

In example 1, the novel and surprising finding is shown according to which neuronal cells have considerably less free thiol groups under physiological conditions than non-neuronal cells. The marking of free thiol groups was effected with the fluorescence dye 5-[and 6-](((chloromethyl-) benzoyl-) amino-) tetramethyl rhodamine (CMTMR). The reactive chloromethyl group of CMTMR reacts with free thiol groups of proteins independent of the type of cells, whereby those are made visible after specific excitation in the UV region.

FIG. 1 shows a view to organotypical hippocampal tissue cuts. Surprisingly, just the decidedly vulnerable neurons of the hippocampus formation (pyramidal cells) show a very low and, hence, hardly detectable content of free thiol groups.

Figure 1B:
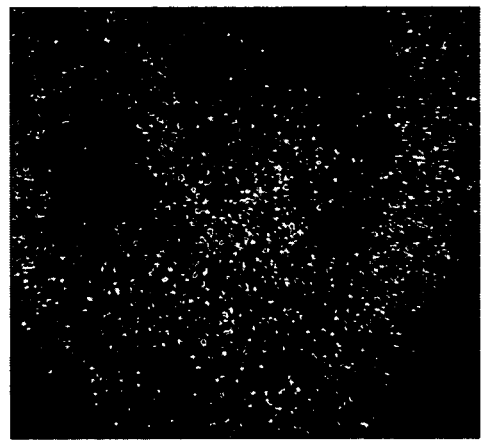
Figure 2A:
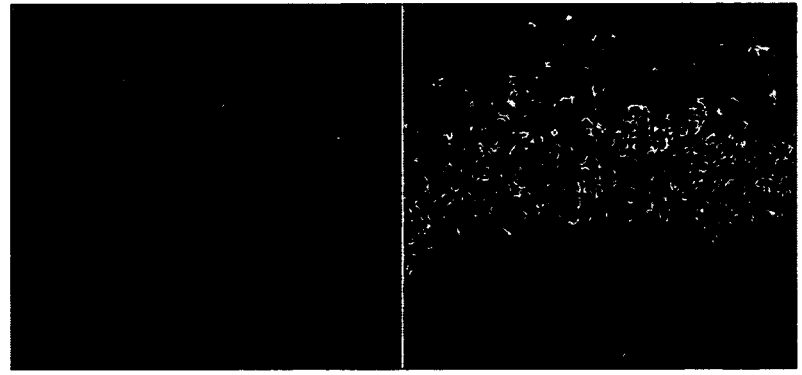
FIGS. 2a and 2b illustrate subject matter similar to that of FIGS. 1a and 1b on a neuronal level.
Figure 2B:

This specifity becomes evident very clearly in FIGS. 1b and 2b. In those Figures, the results of a double marking are shown. In addition to a specific marker for free thiol groups (CMTMR), NeuroTrace (NT) was used as a neuronal marker. FIG. 2a shows the fluorescence of CMTMR (in red color) and of NT (in green color). Both fluorescence signals are not co-localized in the cells, which fact demonstrates that NT and CMTMR are localized in different types of cells largely, i.e. in neuronal or non-neuronal cells, respectively. The FIGS. 1b and 2b show a superposition of both channels.

EXAMPLE 2

Influence of the combination of substances on the survival of neuronal cells after neurodegenerative events For examining the neuroprotective effect of the thiol-reactive substances, the procedure of a transient ischemia for organotypical hippocampal tissue cuts was used [14-16], which procedure was standardized in our laboratory. By such a procedure, there are obtained three-dimensional cultivated explantates having a high prediction value for subsequent clinical experiments. In those tissue cultures containing neuronal as well as non-neuronal cells, highly complex intercellular connections are maintained largely. They are of extraordinary importance for the functionality of the whole CNS. The cerebral tissue cultures are exposed to a degenerative event which results into a death of neuronal cells in analogy to clinical situations.

The tissue cuts (375 μm) were prepared subsequently from the hippocampus of rats (P7). The cultivation of those cut cultures was effected on membrane inserts having a pore size of 0.02 μm. After 10 to 12 days of cultivation (37° C. in an incubator; 3.3% $CO_2$; 98% relative air humidity), the restructuration processes within the tissue cultures were finished, and a clinical relevant neurodegenerative event was simulated on the tissue cuts by means of a transient oxygen/glucose deprivation. The effect of the substanc(es) was measured in the form of a standard damage change (vehicle application).

In FIG. 3, the effect of the combination of α-lipoic acid (10 μg/ml), ambroxol (10 μM) and Enalapril (20 μg/ml) (in the following addressed as "the cocktail") on the survival of neuronal cells after OGD is shown. There was quantified the neuronal damage after a standard OGD with and without the application of the cocktail as well as the damage by the application of the cocktail per se (optional toxicity of the substance). Table 1 summarizes the statistical parameters of the corresponding random tests. The damage is expressed in % of the damaged surface area. In order to obtain such figures, in each tissue cut the whole surface area was compared with the damaged surface area.

TABLE 1

| Specifity | Number | Average Value | Median | SEM |
|---|---|---|---|---|
| Control OGD | 7 | 12.45 | 12.8 | 1.59 |
| Control OGD + Cocktail | 7 | 6.69 | 7.73 | 2.1 |
| Cocktail without OGD | 5 | 0.42 | 0.08 | 0.23 |

Surprisingly, a pronounced and significant reduction of the neuronal damage could be achieved by the application of the combinations of the invention, which are claimed in the claims and comprise the components specified above in detail. The quantification of the neuroprotective effects achieved amounts to about 40 to 45%. Simultaneously, this experiment shows that the combination tested does result into no damage of the neuronal cells without a degenerative event. This is an elemental precondition for the clinical use of the substances or combinations for a therapy or prevention of neurodegenerative diseases.

EXAMPLE 3

Comparison of the combined use of the combination claimed according to the invention with the effects of the single components.

In the course of these experiments, it was detected that an application of the single substances does not result into a significant neuroprotective effect. The experiments are based on the protocol described in Example 2. In the course of the experiments shown in FIGS. 4a to c, the protective effect of the cocktail was compared with the standard damage after OGD and with the effect resulting from an application of the single substances. It results clearly from all experiments that none of the tested single substances alone reduces the damage after a neurodegeneration, while the cocktail is capable of providing a significant protection. Tables 2a to c show the relevant statistical parameters.

TABLE 2a

| Specifity | Number | Average Value | Median | SEM |
|---|---|---|---|---|
| Control OGD | 9 | 11.70 | 10.8 | 1.71 |
| Control OGD + Cocktail | 9 | 7.86 | 5.53 | 2.18 |
| Control OGD + α-Lipoic Acid | 9 | 14.82 | 13.54 | 3.40 |

TABLE 2b

| Specifity | Number | Average Value | Median | SEM |
|---|---|---|---|---|
| Control OGD | 9 | 13.37 | 11.99 | 1.22 |
| Control OGD + Cocktail | 9 | 9.91 | 8.65 | 1.57 |
| Control OGD + Ambroxol | 9 | 10.79 | 8.32 | 1.88 |

TABLE 2c

| Specifity | Number | Average Value | Median | SEM |
|---|---|---|---|---|
| Control OGD | 11 | 13.98 | 12.27 | 1.63 |
| Control OGD + Cocktail | 11 | 9.62 | 7.57 | 1.95 |
| Control OGD + Enalapril | 10 | 11.23 | 8.70 | 1.76 |

In contrast to the cocktail (composition containing α-lipoic acid, ambroxol and ACE inhibitor), neither α-lipoic acid nor ambroxol nor the ACE inhibitor, if applied alone, were capable of reducing the neuronal damage significantly after a transient OGD.

The invention claimed is:

1. A method for therapy of a neurodegenerative disease or ischemia comprising administering to an individual an effective amount of a composition comprising ambroxol or its salts and at least one inhibitor of the angiotension-converting enzyme, wherein the therapy of the neurodegenerative disease or ischemia comprises a synergistic inhibition of neuronal damage.

2. The method according to claim 1, wherein the neurodegenerative disease is selected from the group consisting of ischemic or hemorrhagic stroke, amyotrophic lateral sclerosis, Alzheimer's disease, Parkinson's disease, Hunntington's disease, multiple sclerosis, neurodegeneration of aged people, dementia, cranial cerebral trauma, and Autosomal Dominant Neurohypophyseal Diabetes Insipidus.

3. The method of claim 1, wherein the ischemia is cerebral ischemia resulting from cardiac and cardiovascular insults.

4. The method of claim 1, wherein the composition further comprises α-lipoic acid or its salts or its isomers.

5. The method of claim 1, wherein the composition further comprises pharmaceutically acceptable carriers, additives and/or adjuvants.

6. The method of claim 4, wherein the α-lipoic acid or its salts or its isomers are administered in an amounts of from 30 to 1,200 mg/day, and/or ambroxol or its salts are administered in an amount of from 7.5 to 90 mg/day, and/or at the inhibitor of the angiotensin-converting enzyme is administered in an amount of from 1 to 50 mg/day.

7. The method of claim 6, wherein the α-lipoic acid or its salts or its isomers are administered in an amounts of from 200 to 600 mg/day, and/or ambroxol or its salts are administered in an amount of from 60 to 75 mg/day, and/or at the inhibitor of the angiotensin-converting enzyme is administered in an amount of from 5 to 20 mg/day.

8. The method of claim 1, wherein the composition is administered by a route selected from buccal, pulmonal, nasal, transdermal, intravenous, subcutaneous, intracutaneous, intramuscular, rectal, vaginal and intrathecal administration.

9. The method of claim 1, wherein the composition is administered in the form of tablets, powders, granulates, capsules, solutions, emulsions, suspensions, aerosols, transdermal application systems, suppositories and administration forms having a retarded release of single or all effective agents.

10. A composition comprising ambroxol or its salts and at least one inhibitor of the angiotension-converting enzyme, wherein the composition is capable of synergistically inhibiting neuronal damage.

11. A method for obtaining a synergistic improvement in the survival of neuronal cells after oxygen and/or glucose deprivation in an individual comprising administering to the individual a composition comprising ambroxol, at least one inhibitor of the angiotensin-converting enzyme, and α-lipoic acid.

12. The method of claim 11, wherein the inhibitor of the angiotensin-converting enzyme is selected from the group consisting of captopril, lisinopril, enalapril, ramipril, spirapril, imidapril and moexipril.

13. The method of claim 12, wherein the angiotensin-converting enzyme is elanapril.

14. The method of claim 11, wherein the composition further comprises a pharmaceutically acceptable carrier.

* * * * *